(12) United States Patent
Ryan

(10) Patent No.: US 11,219,500 B2
(45) Date of Patent: Jan. 11, 2022

(54) AEROSOL REDUCTION SYSTEMS AND METHODS

(71) Applicant: Perio Dome Inc, Belton, MO (US)

(72) Inventor: Lara L. Ryan, Belton, MO (US)

(73) Assignee: Perio Dome Inc, Belton, MO (US)

( * ) Notice: Subject to any disclaimer, the term of this patent is extended or adjusted under 35 U.S.C. 154(b) by 0 days.

(21) Appl. No.: 17/230,209

(22) Filed: Apr. 14, 2021

(65) Prior Publication Data

US 2021/0378778 A1  Dec. 9, 2021

Related U.S. Application Data

(60) Provisional application No. 63/035,944, filed on Jun. 8, 2020.

(51) Int. Cl.
| | |
|---|---|
| *A61B 90/00* | (2016.01) |
| *A61C 17/06* | (2006.01) |
| *A61B 90/50* | (2016.01) |
| *A61M 1/00* | (2006.01) |

(52) U.S. Cl.
CPC .............. *A61B 90/05* (2016.02); *A61B 90/50* (2016.02); *A61C 17/06* (2019.05); *A61M 1/80* (2021.05); *A61M 2205/7536* (2013.01)

(58) Field of Classification Search
CPC ..... A61C 17/06; A61C 17/065; A61C 17/135; A61C 17/08; A61C 19/007; B08B 15/04; A61B 90/05; A61B 90/50; A61M 1/80; A61M 1/64; A61M 1/71; A61M 2205/7536; A61M 16/009; A61M 2209/082; A61M 2209/084; Y10S 128/91

See application file for complete search history.

(56) References Cited

U.S. PATENT DOCUMENTS

| | | | | |
|---|---|---|---|---|
| 3,537,447 | A * | 11/1970 | Gauthier ................ | A61G 15/14 128/847 |
| 38,133,092 | | 5/1974 | Foster | |
| 4,038,913 | A * | 8/1977 | Earley .................... | A45D 44/02 454/64 |
| 4,446,861 | A * | 5/1984 | Tada ...................... | A61C 19/00 128/863 |
| 5,636,627 | A * | 6/1997 | Rochester ........... | A61M 16/009 128/205.27 |
| 9,888,989 | B2 * | 2/2018 | Ishizaki ................ | A61C 17/08 |
| 2002/0150861 | A1 * | 10/2002 | Lu ........................ | A61C 19/007 433/91 |

(Continued)

OTHER PUBLICATIONS

International Search Report and Written Opinion in corresponding PCT/US2021/027224, dated Jul. 29, 2021.

*Primary Examiner* — Jacqueline T Johanas
*Assistant Examiner* — Shannel Nicole Belk
(74) *Attorney, Agent, or Firm* — Hovey Williams LLP

(57) ABSTRACT

A system for reducing aerosols emitted from a patient on which a medical procedure is being performed. The system comprises a transparent dome and an adapter assembly configured to releasably support the dome. The system additionally comprises a support assembly configured to support the adapter assembly and the dome. The support assembly is adjustable such that the dome can be selectively positioned over an intended body area of the patient and block aerosols emitted from the intended body area.

18 Claims, 11 Drawing Sheets

(56) References Cited

U.S. PATENT DOCUMENTS

| | | | |
|---|---|---|---|
| 2004/0158120 A1* | 8/2004 | Paranjpe | A45D 29/00 600/21 |
| 2011/0108143 A1* | 5/2011 | Caluori | A61C 17/0202 137/561 R |
| 2012/0288821 A1* | 11/2012 | Meyer | A61C 19/007 433/92 |
| 2013/0196585 A1* | 8/2013 | Hedlund | F16L 27/0861 454/63 |
| 2013/0253358 A1 | 9/2013 | Phillips | |
| 2016/0375183 A1* | 12/2016 | Chen | A61M 1/88 128/848 |

* cited by examiner

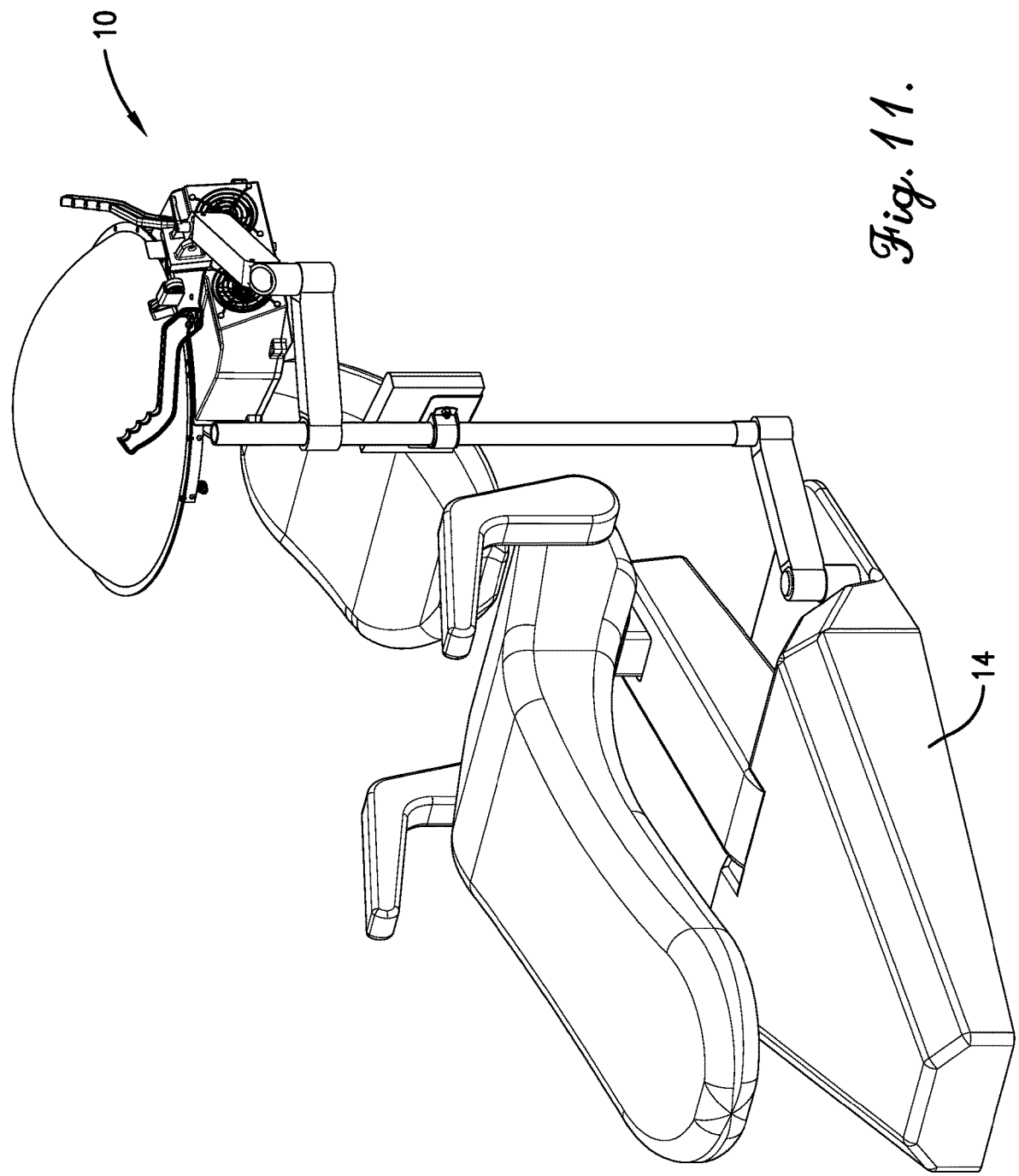

AEROSOL REDUCTION SYSTEMS AND METHODS

CROSS-REFERENCE TO RELATED APPLICATIONS

The present non-provisional patent application claims the priority benefit of U.S. Provisional Patent Application Ser. No. 63/035,944, filed Jun. 8, 2020, entitled AEROSOL REDUCTION DOME FOR DENTAL PROCEDURES, with the entirety of the above-identified provisional patent application being incorporated herein by reference.

BACKGROUND OF THE INVENTION

Field of the Invention

The present invention relates to systems and methods for reducing aerosols. Such systems and methods may, for instance, be used during medical procedures (e.g., during dental procedures) to reduce aerosols generated during such procedures.

Description of Related Art

In dentistry, aerosols are commonly produced during many procedures. Dental care providers typically wear a mask to cover their mouth and nose as well as glasses to cover their eyes to minimize transmission of bodily fluids from patients during dental procedures. In some cases, dental providers wear full face mask coverings or shields. With the new pandemic caused by SARS-CoV2, dentists, patients, and dental care providers are particularly vulnerable to being exposed to potential aerosols, including from COVID-19 positive patients and/or the dental care professionals. This is because these procedures require working within the oral cavity of the patient. Thus, unlike other healthcare procedures, the risks cannot be minimized by requiring the patient to wear a mask.

SUMMARY OF THE INVENTION

The present invention is broadly concerned with a system for reducing aerosols emitted from a patient on which a medical procedure is being performed. The system comprises a transparent dome and an adapter assembly configured to releasably support the dome. The system additionally comprises a support assembly configured to support the adapter assembly and the dome. The support assembly is adjustable such that the dome can be selectively positioned over an intended body area of the patient and block aerosols emitted from the intended body area.

Embodiments of the present invention also include methods of using an aerosol reduction system during a medical procedure. Such a method may include the step of providing a system comprising a transparent dome, an adapter assembly configured to releasably support the dome, and a support assembly configured to support the adapter assembly and the dome. The exemplary method may additionally include the step of actuating the support assembly such that the dome is positioned over an intended body area of a patient. The method may further include the step of blocking, via the dome, aerosols emitted from the body area of the patient.

This summary is not intended to identify essential features of the present invention, and is not intended to be used to limit the scope of the claims. These and other aspects of the present invention are described below in greater detail.

BRIEF DESCRIPTION OF THE DRAWINGS

Embodiments of the present invention are described in detail below with reference to the attached drawing figures, wherein:

FIG. 11 is another environmental view of a system for reducing aerosols during a medical procedure, with the system being connected to a dental chair.

Figure 1:
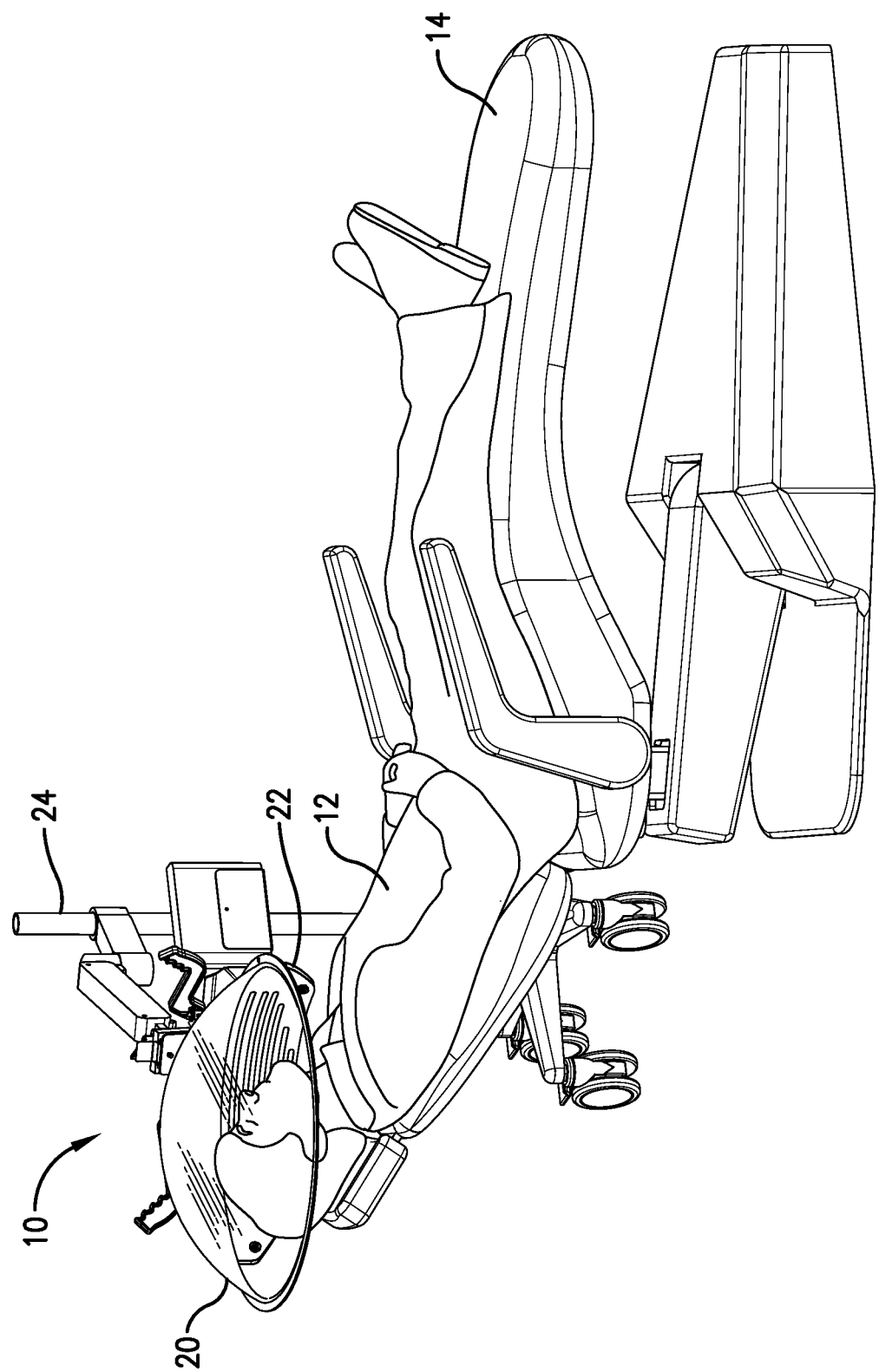
FIG. 1 illustrates an environmental view of a system for reducing aerosols during a medical procedure, with the system particularly being used on a patient undergoing a dental procedure.

The figures are not intended to limit the present invention to the specific embodiments they depict. While the drawings do not necessarily provide exact dimensions or tolerances for the illustrated structures or components, the drawings are to scale with respect to the relationships between the components of the structures illustrated in the drawings.

DETAILED DESCRIPTION

The following detailed description of embodiments of the invention references the accompanying figures. The embodiments are intended to describe aspects of the invention in sufficient detail to enable those with ordinary skill in the art to practice the invention. The embodiments of the invention are illustrated by way of example and not by way of limitation. Other embodiments may be utilized and changes may be made without departing from the scope of the claims. The following description is, therefore, not limiting. The scope of the present invention is defined only by the appended claims, along with the full scope of equivalents to which such claims are entitled.

In this description, references to "one embodiment," "an embodiment," or "embodiments" mean that the feature or features referred to are included in at least one embodiment of the invention. Separate references to "one embodiment," "an embodiment," or "embodiments" in this description do not necessarily refer to the same embodiment and are not mutually exclusive unless so stated. Specifically, a feature, component, action, step, etc. described in one embodiment may also be included in other embodiments, but is not necessarily included. Thus, particular implementations of the present invention can include a variety of combinations and/or integrations of the embodiments described herein.

Figure 2:
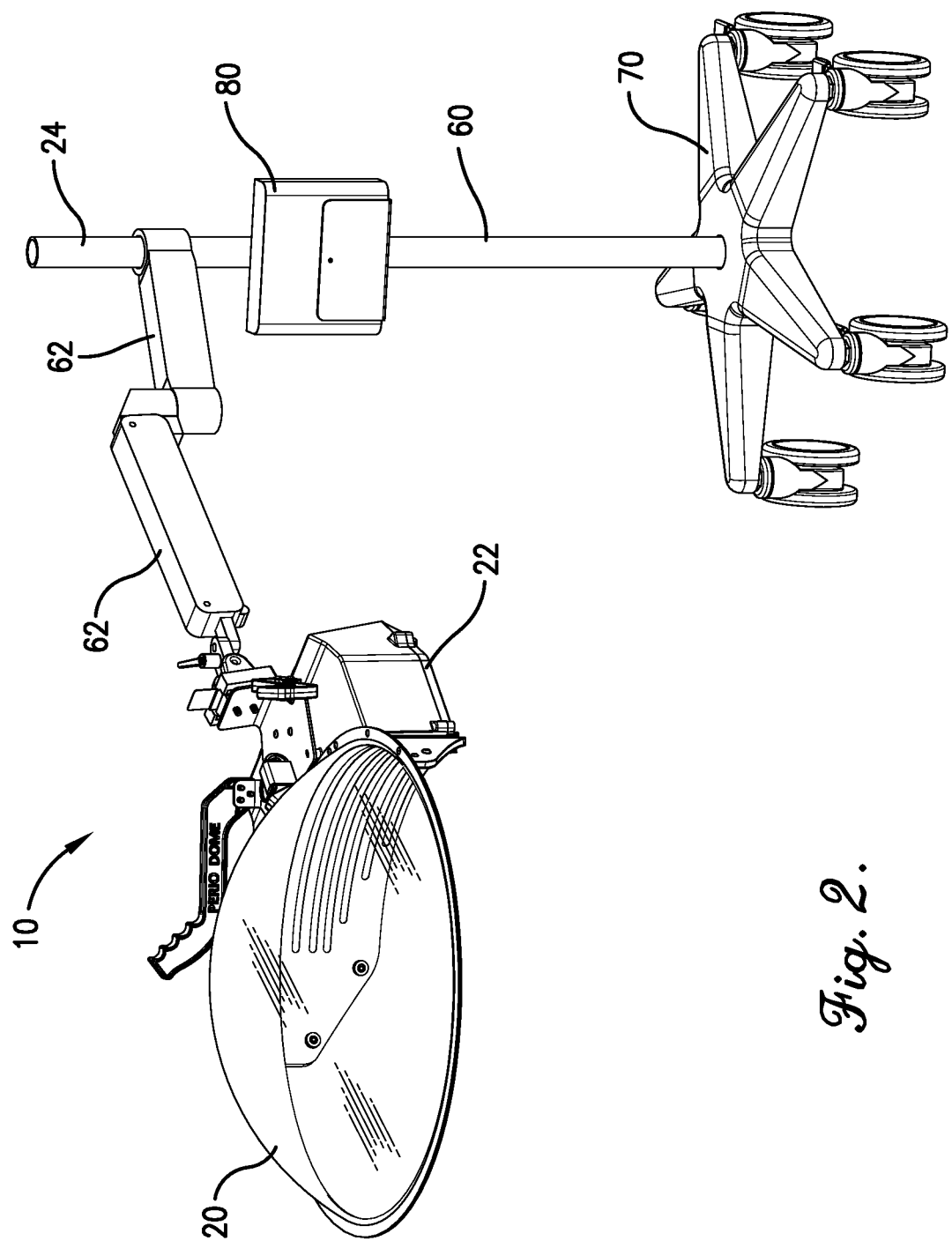
FIG. 2 is a perspective view of the system from FIG. 1.
Figure 3:
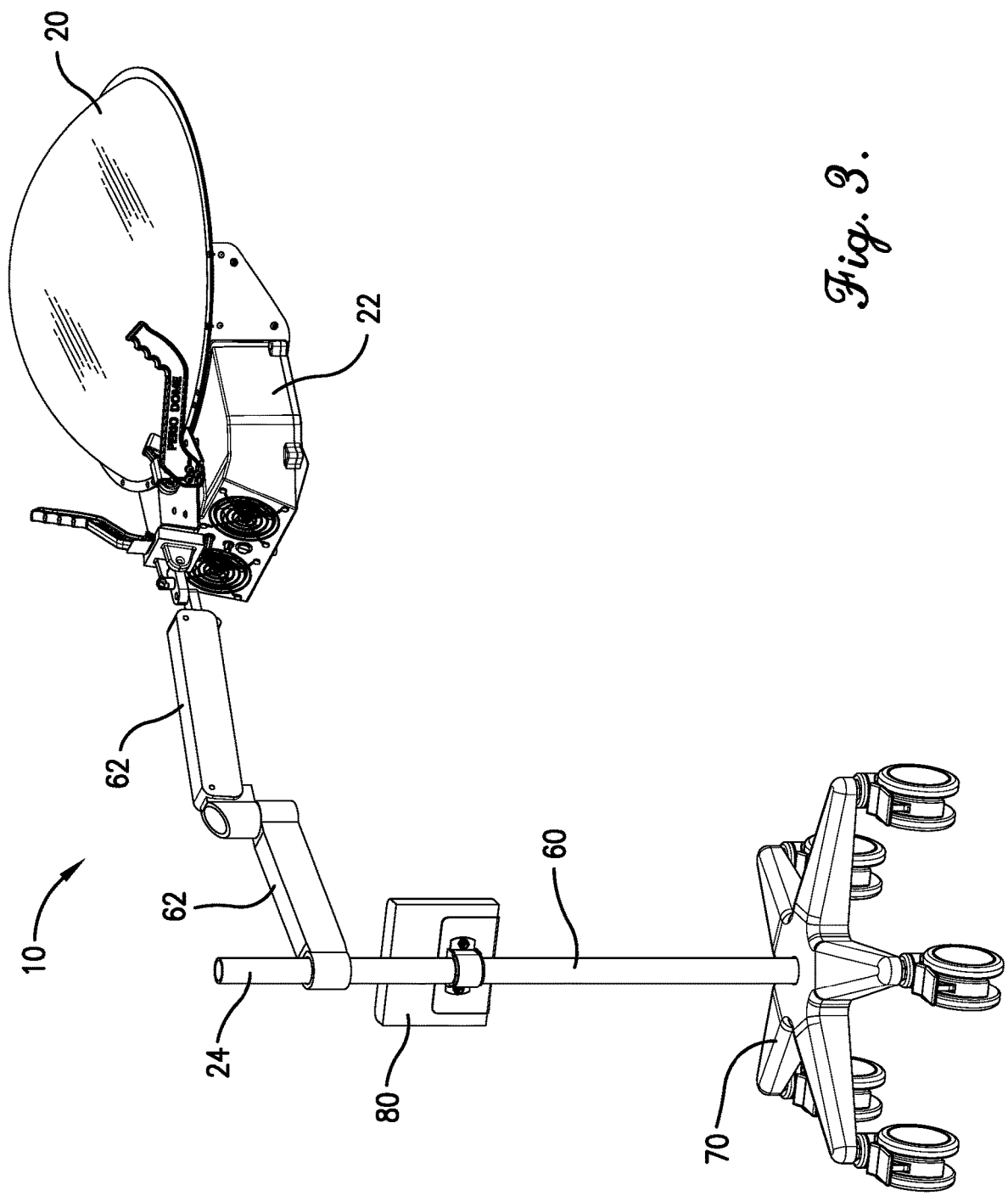
FIG. 3 is another perspective view of the system from FIGS. 1 and 2.

The present invention is concerned with an apparatus, systems, and/or methods for reducing aerosols during medical procedures. An exemplary system 10 is illustrated in FIG. 1, with the system 10 being used during the performance of a dental procedure in which a patient 12 is sitting/lying on a dental chair 14. Broadly, as shown in FIGS. 1-3, the system 10 may comprise a transparent dome 20, an adapter assembly 22 configured to releasably support the dome 20, and a support assembly 24 configured to support the adapter assembly 22 and the dome 20. As will be described in more detail below, the support assembly 24 is adjustable such that the dome 20 can be selectively positioned over an intended body area of the patient 12. For example, as illustrated in FIG. 1, the system 10 may be configured/adjusted such that the dome 20 is positioned over the head of the patient 12 during a dental procedure. As such, the system 10, including the dome 20, is beneficially configured to block and/or collect aerosols emanating from the patient's 12 mouth so as to reduce the spread of contamination (e.g., SARS-CoV2) associated with aerosols generated and/or emitted from the body area of the patient. As a further benefit, because the dome 20 is transparent, medical personnel can perform their necessary procedures (e.g., dental procedures) on the intended body area of the patient 12 (e.g., dental procedures on the patient's 12 head, mount, and/or teeth) by looking through the dome 20 at the intended body are of the patient 12 all while the dome 20 is preventing aerosols from being exposed to the medical personnel.

Figure 4:
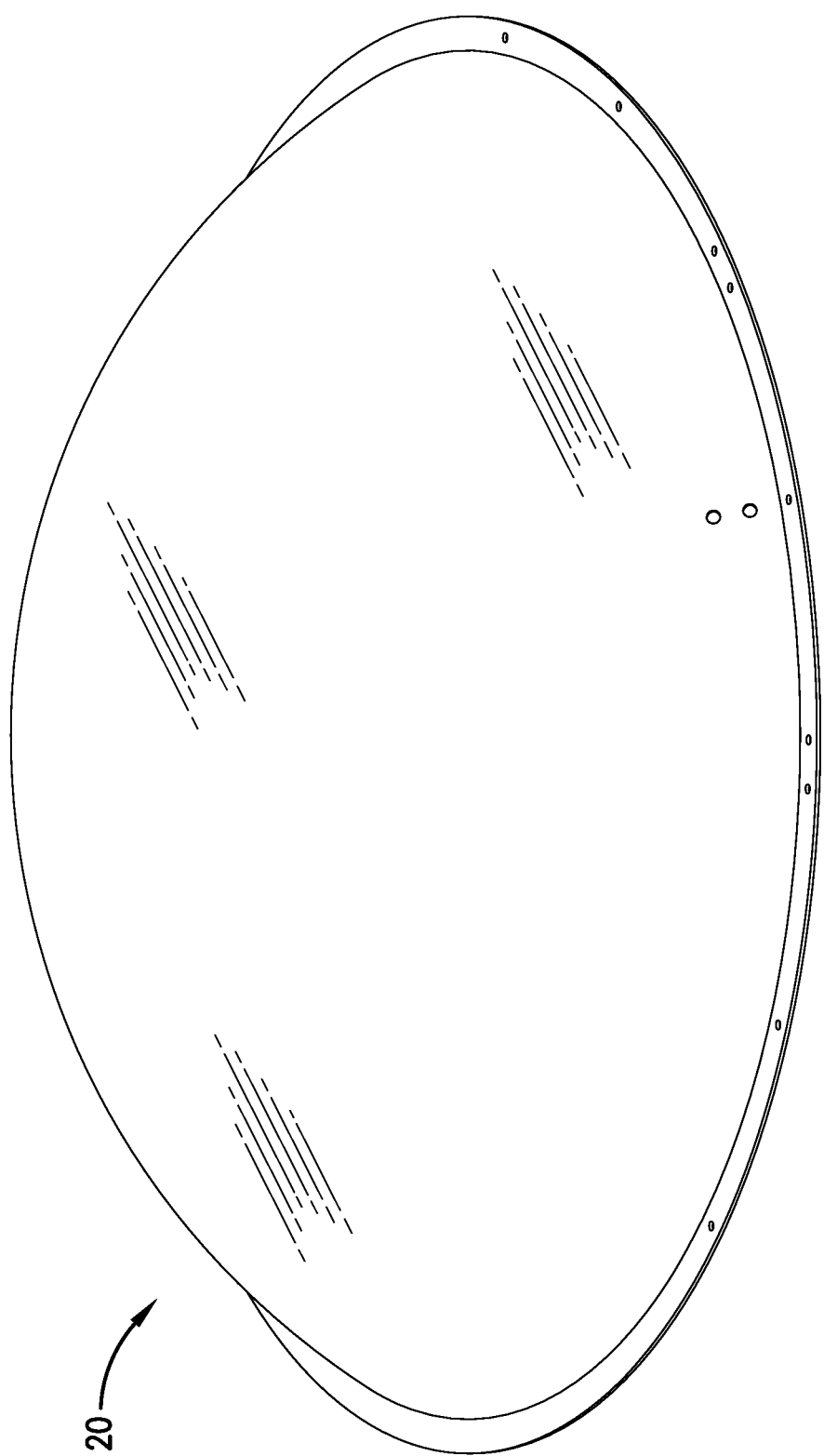
FIG. 4 is a perspective view of a transparent dome from the system of FIGS. 1-3.
Figure 5:
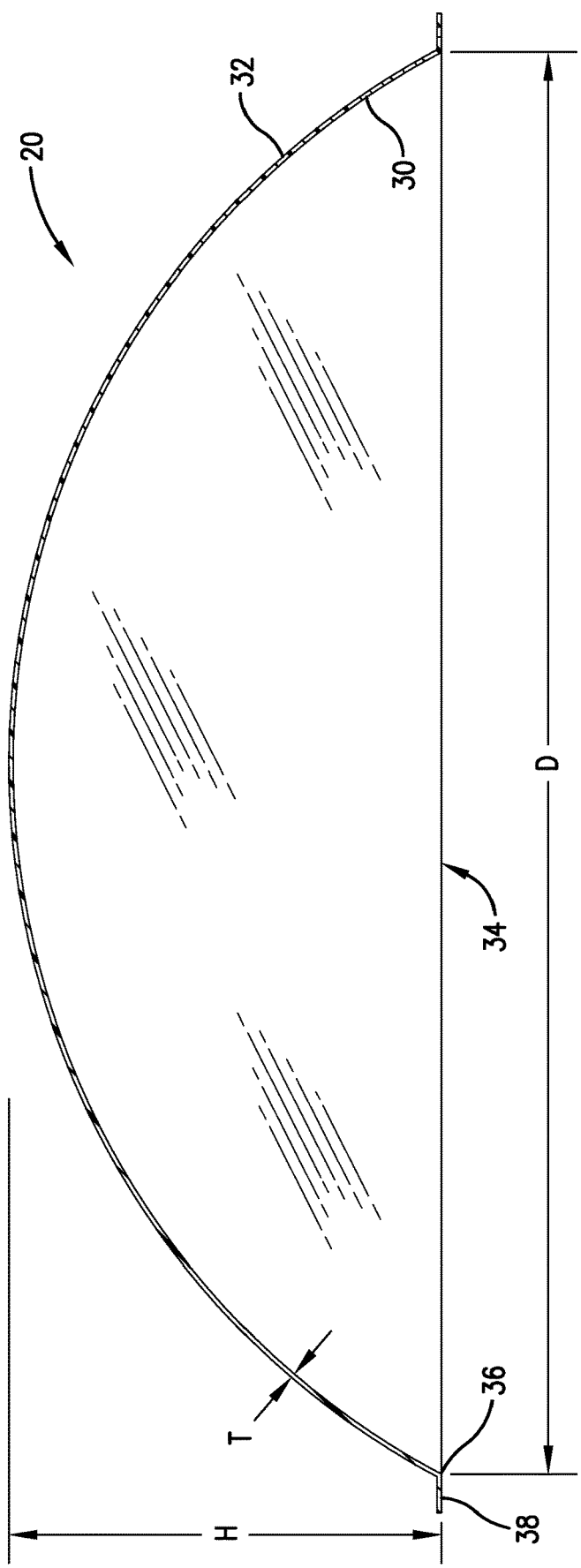
FIG. 5 is a cross-section of the dome from FIG. 4.

In more detail, the dome 20 may be made of transparent material, such as clear plastic (e.g., acrylics, polymethylmethacrylate, Plexiglass, polyethylene terephthalate (PET or APET)), or glass. As used herein, the term transparent material is used to mean a material that permits visual light to at least partly pass therethrough, such that a human observer on one side of the material can observe objects positioned on an opposite side of the material. As shown in FIGS. 4 and 5, the dome 20 will generally comprise a bowl-shaped body, such as a hollow hemisphere, a hollow partial sphere (e.g., a half sphere), or a non-symmetric bowl-shaped body. For example, as shown in FIG. 5, the dome 20 may comprise a shell in the form of hollow partial sphere. However, the dome 20 may have other shapes, some which are described below in more detail.

Remaining with FIG. 5, the dome 20 may be in the form of a bowl-shaped body comprising a shell or wall with an inner surface 30 and an outer surface 32. The inner surface 30 may be concave, while the outer surface 32 may be convex. As such, the dome 20 will be configured with an open end 34, such that a body area of a patient (e.g., the head of the patient 12) can be positioned through the open end and at least partially within the dome 20. Specifically, the concave inner surface 30 may define an inner bowl of the dome 20 (i.e., the area between the inner surface 30 and the open end 34 of the dome 20), such that when the dome 20 is positioned above the patient's head, face, oral cavity, or other body area, the patient's head, face, oral cavity, or other body area can be at least partially received within the inner bowl of the dome 20. However, in other embodiments, the dome 20 may simply be positioned above the intended body area of the patient, with out the body area of the patient being received within the inner bowl.

Remaining with FIG. 5, the thickness "T" of the shell/wall of the dome body may be between 0.004 and 0.4 inches (between 0.1 mm and 10 mm), preferably from about 0.04 and 0.3 inches (from about 1 mm to about 8 mm), more preferably from about 0.1 and 0.3 inches (from about 2.5 mm to about 8 mm), and/or about 0.125 inches (3.175 mm).

In some alternative embodiments, the dome 20 may comprise a double-wall, as opposed to a single wall. Specifically, the dome 20 may comprise two or more adjacent/parallel walls that define the bowl shape.

The dome 20 may comprise an annular edge 36 defining a perimeter of the open end 34. The dome 20 may also include an annular flange 38 that extends laterally from the outer surface 32 adjacent the annular edge 34. The annular flange 38 may have a length of about 0.5 inches, such that the annular flange 38 that extends laterally from the outer surface 32 adjacent the annular edge 34 a distance of about 0.5 inches. As will be described in more detail below, the annular flange 38 may be configured to assist in securing the dome 20 to the adapter assembly 22. In some embodiments, the edge 34 of the dome 20 may not include the annular flange 38. As such, the dome may, instead, comprise a continuous smooth edge surface with no flange or lip.

In some embodiments, the dome 20 can be sized and shaped such that the inner bowl is configured for receiving the head or face of a patient through the open end 34 and within the inner bowl of the dome 20, with the inner surface 30 (i.e., the concave surface) in opposed face-to-face relationship with the patient. The open end 34 of the dome 20 may have a diameter "D" that is about 20 inches, and/or that ranges from about 12 to 45 inches, from about 12 to about 40 inches, from about 12 to about 36 inches, or from about 12 to about 30 inches. The height "H" of the dome 20, as measured from the edge 36 of the open end 34 to the top of the outer surface 32 (e.g., the top of the convex surface) may be about 6 inches, and/or can range from about 4 to about 30 inches, from about 6 to about 30 inches, from about 8 to about 25 inches, from about 9 to about 20 inches, or from about 10 to about 20 inches. It will be appreciated that more shallow dome 20 configurations can be used without departing from the scope of the invention. In one or more embodiments, the diameter "D" may be approximately 1.2 times the height "H" of the dome 20, or 1.5 times the height "H" of the dome 20, or 1.8 times the height "H" of the dome 20, or 2 times the height "H" of the dome 20, or 3 times the height "H" of the dome 20, or 3.5 times the height "H" of the dome 20, or 4 times the height "H" of the dome 20, and/or may be between approximately 1.2 and 4 times the height "H" of the dome 20, or between approximately 2 and 3.5 times the height "H" of the dome 20.

As described above, the dome 20 may be formed in a generally circular shape, such as a half sphere. However, in other embodiments, the dome 20 may have other shapes, such as having an oval or oblong shape. In some embodiments, the dome 20 may have a non-symmetric shape, such as bowl shape with one or more bulging portions. Furthermore, the outer surface 32 may not necessarily be convex. For instance, the dome 20 may be formed with a significant thickness such that the outer surface 32 can be non-curved (e.g., flat) or may otherwise have a shape that does not correspond with the inner surface 30. Regardless, the dome 20 will generally include an inner surface 30 that is concave in shape, so as to be configured to block or collect aerosols emitted from a patient. It is contemplated, however, that while inner surface 30 may be generally concave, the particular shape of the inner surface 30 may vary. For instance, the inner surface 30 may be entirely round/spherical, or alternatively, may flatten out in the center while having rounded edges.

In certain embodiments, the dome 20 may be monolithic comprising a single, continuous wall (or the dome 20 may be monolithic comprising a double wall, or any number of walls). It is contemplated, however, within the scope of the present invention that the dome 20 may be provided in two or more sections as well, with these sections being operatively associated with each other to form the dome 20. For example, the dome 20 can be made of two separate sections (e.g., substantially equal complementary halves) that can be connected to each other to form the dome 20).

Figure 6:
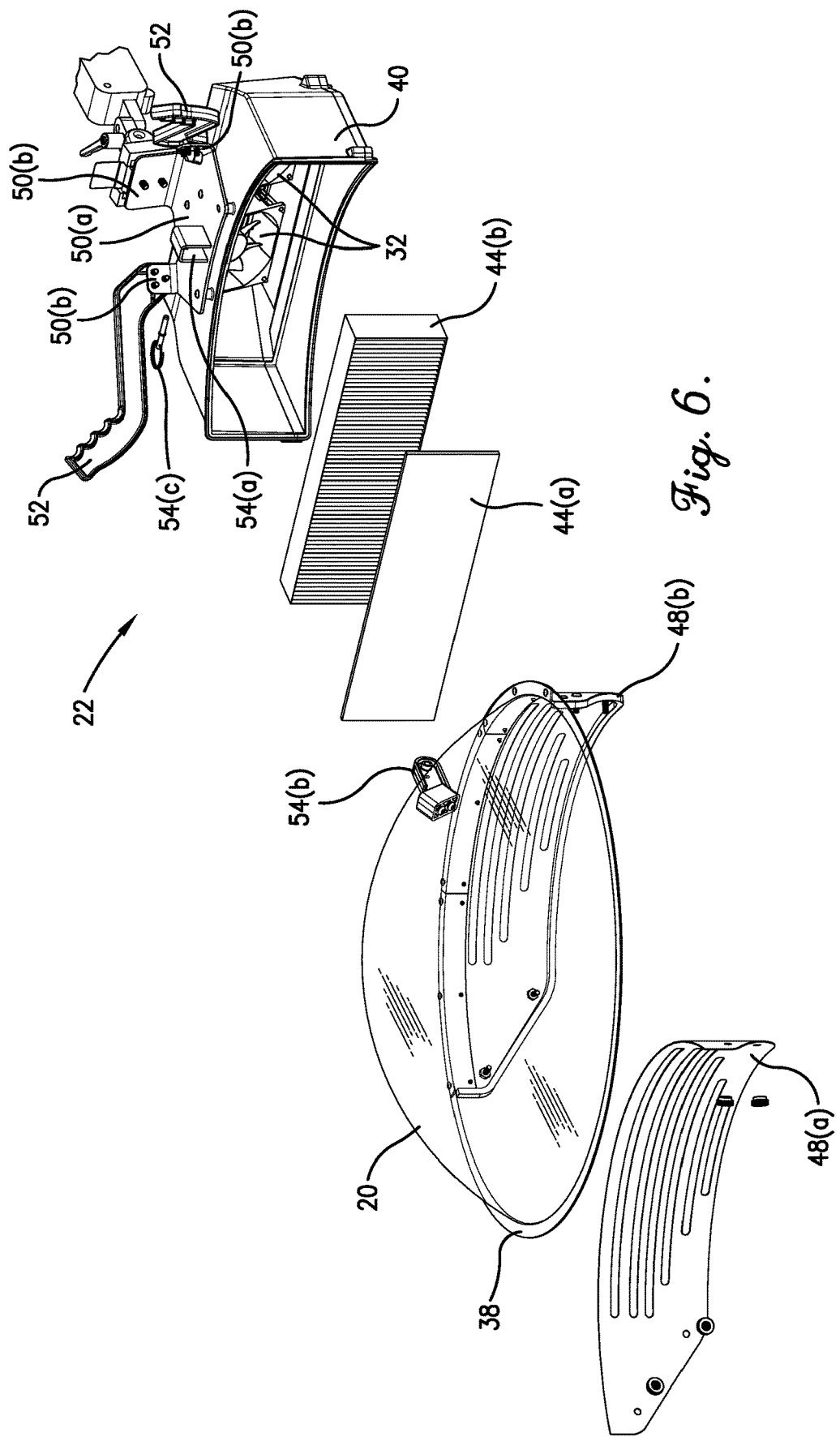
FIG. 6 is an exploded view of a portion of the system from FIGS. 1-3.
Figure 7:
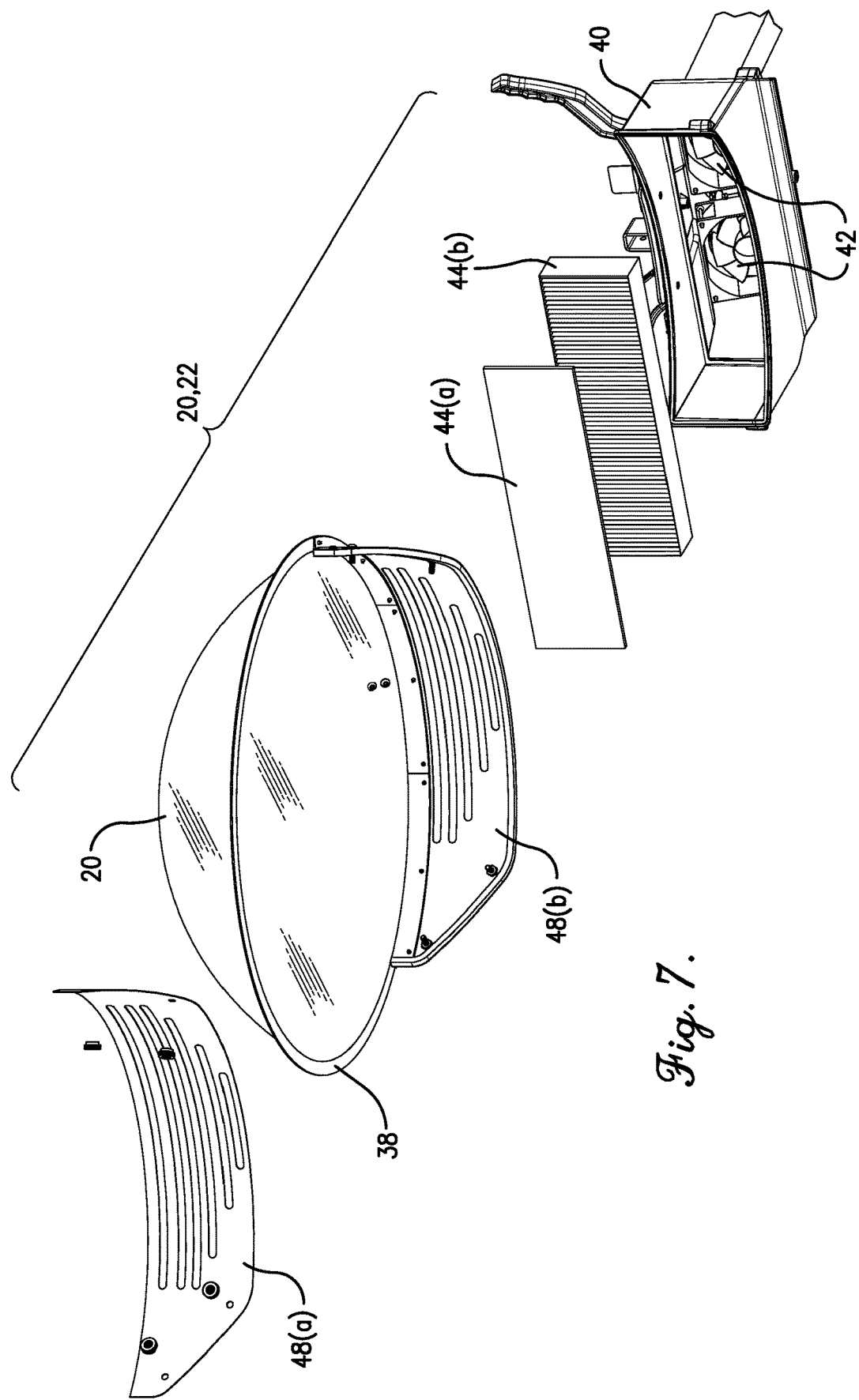
FIG. 7 is another exploded view of the portion of the system shown in FIG. 6.
Figure 8:
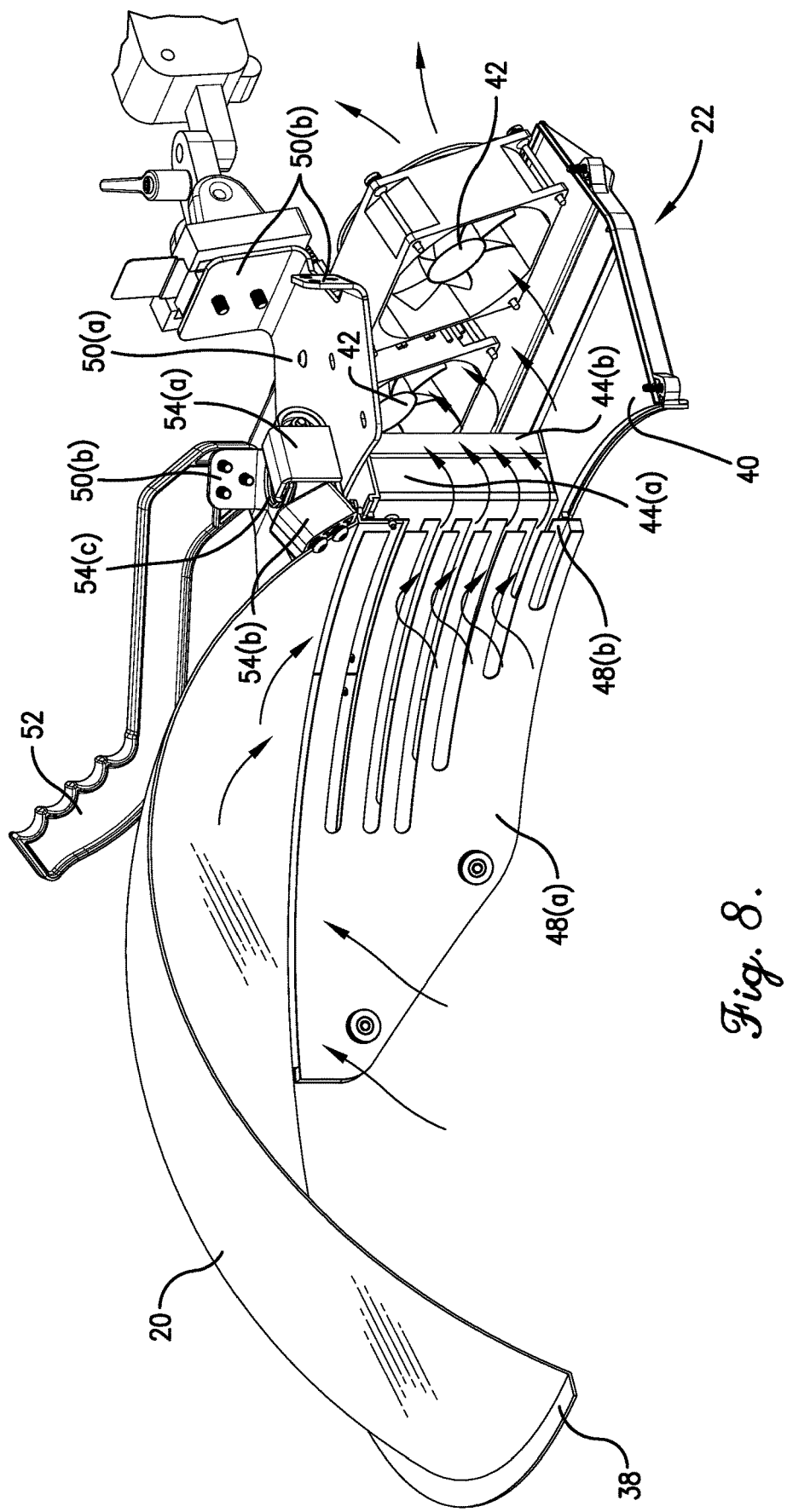
FIG. 8 is a partial view of an adapter assembly and a dome from the system of FIGS. 1-3, with a portion of the dome and the adapter assembly removed to illustrate a path of air and/or aerosols traveling through the system.

Turning to FIGS. 6-8, the dome 20 and the adapter assembly 22 are shown in more detail. The adapter assembly 22 may comprise a housing 40 that presents an interior space. The adapter assembly 22 may additionally comprise one or more fans 42 or other pneumatic components (e.g., pumps) configured to generate negative air pressures so as to cause air to flow through the housing 40. For instance, as illustrated in FIG. 8, the fans 42 may be positioned at a rear of the housing 40 and configured to draw air through an opening forming an inlet of the housing 40 (e.g., with the inlet located at the front of the housing 40), through the interior space of the housing 40, and through the fans 42 themselves out of an opening forming an outlet of the housing 40 (e.g., with the outlet located at the rear of the housing 40). As will be described in more detail below, and as illustrated in FIG. 8, when the dome 20 is secured to the adapter assembly 22, the inlet to the housing of the adapter assembly 22 is positioned adjacent to the edge 36 of the dome 20. As such, the fans 42 of the adapter assembly 22 are configured to draw air (and any associated aerosols) from the area under the dome 20 (e.g., where the patient's body area may be positioned) through and out the adapter assembly 22. As such, the dome 20 can block aerosols emitted from a patient, and the adapter assembly 22 can draw such aerosols into the adapter assembly 22 via the fans 42.

In some embodiments, the adapter assembly 22 may include one or more filters for filtering and/or purifying the air flowing through the housing 40. For example, as illustrated in FIGS. 6-8, the adapter assembly may include a first filter 44(a) and a second filter 44(b) supported within the housing 40 (e.g., adjacent to the inlet of the housing 40) and configured to filter or purify the air and/or aerosols flowing through the housing 40. In some embodiments, the first filter 44(a) may comprise a carbon-based filter that includes activated carbon/charcoal configured to remove impurities, particulates, and/or aerosols from the air flowing through the adapter assembly 22. In some embodiments, the second filter 44(b) may comprise a high-efficiency particulate air (HEPA) filter configured to remove impurities, particulates, and/or aerosols from the air flowing through the adapter assembly 22. HEPA filters are configured to trap at least 99.97 percent of particulates that are least 0.3 microns in size. In some additional embodiments, one or more of the filters (e.g., filter 44(a) or 44(b)) may comprise an ultraviolet (UV) light filter configured to disinfect air by destroying microorganisms (e.g., bacteria or viruses) contained within the air and/or aerosols traveling through the adapter assembly 22.

Figure 9:
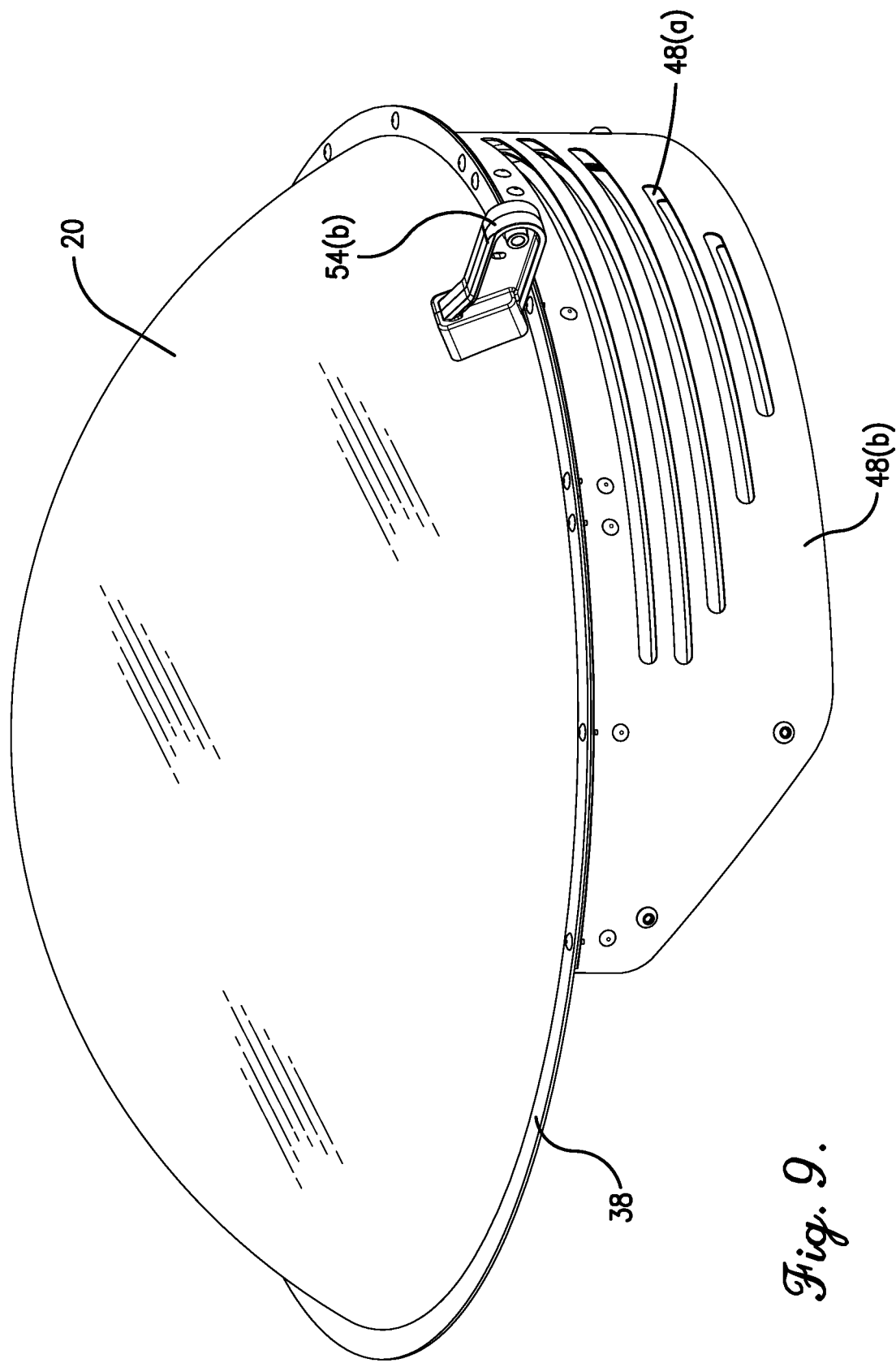
FIG. 9 is a perspective view of a dome of the system of FIGS. 1-3 being separated from main portions of an adapter assembly of the system.
Figure 10:
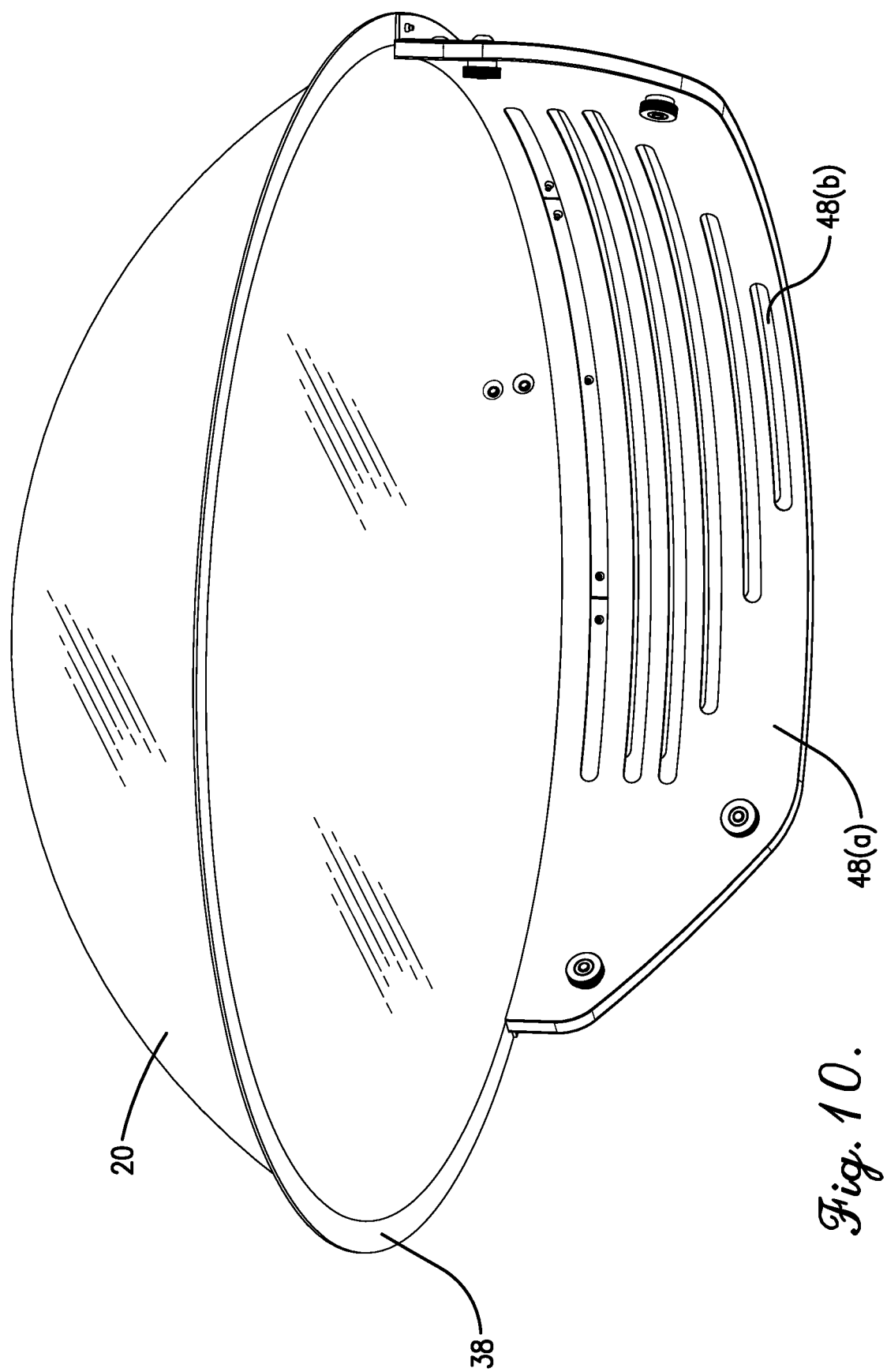
FIG. 10 is another perspective view of the separated dome from FIG. 9.

The adapter assembly 22 may also comprise a baffle assembly configured to regulate airflow through the housing 40. For example, as shown in FIGS. 6-8, the baffle assembly may comprise a first baffle plate 48(a) and a second baffle plate 48(b), each comprising a curved plate with a plurality of horizontal openings through which air is configured to flow. The baffle assembly may be secured to the dome 20, such as via fasteners that extend through the annular flange 38 of the dome 20 and into the baffle assembly. For instance, the second baffle plate 48(b) may secured to the dome 20 via fasteners that extend through the annular flange 38 and into the second baffle plate 48(b). In addition, the first baffle plate 48(a) may be secured to the second baffle plate 48(b) via fasteners that extend through each of the first and second baffle plates 48(a) and 48(b). The first and second baffle plates 48(a) and 48(b) may have curved shapes that generally match the annular flange 38 (or the annular edge 36) of the dome 20 so as to facilitate the coupling between the dome 20 and the baffle assembly, as illustrated in FIGS. 9 and 10. Furthermore, as shown in FIG. 8, the baffle assembly may be releasably secured to the front of the housing 40 of the adapter assembly 22, such as via one or more friction fit elements, such as snap fit elements. To facilitate the connection between the housing 40 and the baffle assembly, the inlet of the housing 40 may also have a curved shape that corresponds with the baffle plates 48(a), 48(b), and thus the annular edge/flange 36, 38 of the dome 20. The horizontal openings of the baffle plates 48(a), 48(b) are particularly configured (e.g., in size, shape, and position) to regulate efficient airflow through the housing 40. Too restrictive airflow can overload the fans 42. In contrast, too restrictive airflow can cause too low of airspeeds, which may result in poor air distribution through the housing 40 (including through the filters).

Furthermore, the adapter assembly 22 may comprise a bracket assembly, as perhaps best illustrated in FIGS. 6 and 8, which is configured to secure the dome 20 and the support assembly 24 to the adapter assembly 22. The bracket assembly may comprise a base plate 50(a) that is secured to a surface of the housing 40 via fasteners, such as to a top surface of the housing 40. The bracket assembly may additionally comprise one or more extension plates 50(b) that extend generally perpendicularly from the base plate 50(a). Such extension plates 50(b) may be used to connect various components of the system 10 to the bracket assembly and/or to the adapter assembly 22. For example, one vertically-oriented extension plate 50(b) (e.g., positioned at a rear of the bracket assembly) may be used to secure the support assembly 24 to the bracket assembly. In addition, a pair of vertically-oriented extension plates 50(b) (e.g., positioned at either lateral side of the bracket assembly) may be used to secure handles 52 to the bracket assembly. Such handles 52 may be grasped by the hands of a user of the system 10 to shift a position of the dome 20 and/or the adapter assembly 22, such that the dome 20 can be manually positioned over an intended body area of the patient 12.

In certain embodiments, the bracket assembly may include a latching unit that permits the dome 20 to be releasably secured to the bracket assembly and/or to the adapter assembly 22. In some embodiments, as illustrated in FIGS. 6 and 8, the latching unit may comprise a receiving element 54(a) that extends generally perpendicularly from the base plate 50(a). For example, the receiving element 54(a) may comprise a channel of material that extends vertically upward from the base plate 50(a) and presents a receiving space. The latching unit may additionally comprise a locking shaft 54(b), which may be in the form of an elongated protrusion configured to be received in the receiving space presented by the receiving element 54(a). A first end of the locking shaft 54(b) may be secured to the dome 20 such as via fasteners that extend through holes formed in the dome 20 and into engagement with the locking shaft 54(b). As illustrated in the figures, the locking shaft 54(b) may extend from the side of the dome 20, at the outer surface 32 of the dome 20, at a position adjacent to the annular edge 36 of the dome 20. However, in other embodiments, the locking shaft 54(b) may extend from other locations on the dome 20, such as from a position adjacent the top (e.g., the apex) of the outer surface 32 of the dome 20 or from a position on the inner surface 30 of the dome 20. The locking shaft 54(b) may also extend from the dome 20 at various angles.

To secure the dome 20 to the adapter assembly 22, the locking shaft 54(b) can be inserted within the receiving space presented by the receiving element 54(a). The locking shaft 54(b) may be held in place within the receiving space by a pin 54(c) or another element inserted within the locking shaft 54(b) and configured to hold the locking shaft 54(b) in place. To remove the dome 20 from the adapter assembly 22, the pin 54(c) may be removed from the locking shaft 54(b) and the locking shaft 54(b) can be removed from within the receiving space presented by the receiving element 54(a). In alternative embodiments, the dome 20 may be attached to the adapter assembly 22 and/or the support assembly 24 in a variety of configurations, including via clips, threaded or bolt-type attachments, and clamps, including spring actuated or spring held type clips or clamps, and the like.

As illustrated by FIGS. 2 and 3, the support assembly 24 may comprise one or more posts, rods, and/or articulating arms configured to support the dome 20 and/or adapter assembly 22. The support assembly 24 is further configured to be actuated vertically and/or rotated about one or more vertical and/or horizontal axes, so as to correspondingly adjust a position of the dome 20 and/or adapter assembly 22. For example, the support assembly 24 may comprise a generally vertical main post 60 that supports one or more articulating arms 62. For example, as shown in FIGS. 2 and 3, the support assembly 24 may include two articulating arms 62, with a first articulating arm 62 extending from the main post 60, and a second articulating arm 62 extending from the first articulating arm and into engagement with the adapter assembly 22. The first articulating arm 62 may be configured to shift vertically (upward/downward) along the main post 60, so as to shift the vertical position of the dome 20 and/or the adapter assembly 22. The first articulating arm 62 may also be configured to rotate about a vertical axis presented by the main post 60, so as to shift the lateral/longitudinal position of the dome 20 and/or the adapter assembly 22. The second articulating arm 62 may also be configured to rotate about a vertical axis presented by the connection with the first articulating arm 62, so as to further enhance the ability to shift the lateral/longitudinal position of the dome 20 and/or the adapter assembly 22. The connection between the second articulating arm 62 and the adapter assembly 22 may provide for rotation about a vertical and/or horizontal axis so as to permit the position of the dome 20 and/or the adapter assembly 22 to shift lateral/longitudinal and/or to tilt upward and downward.

As such, the support assembly 24 can be used to position and hold the dome 20 as needed over the intended body area of the patient 12 (e.g., the head or oral cavity of the patient 12). The support assembly 23 may be embodied as various flexible arm configurations, including articulating arms with a plurality of adjacent segments that can be bent, rotated, and adjusted at a wide variety of angles and positions. Other flexible arm arrangements include those with substantially straight arm portions connected via distinct joints, such that the arm is only flexible around the joint. In some embodiments, the flexible arm can include structure so that it can be locked into place. In other embodiments, the flexible arm includes adequate friction between/within the segment or joints to be maintained in a desired position unless affirmatively moved. In some embodiments, the position of the dome 20 and arm movement can be controlled manually by physically positioning the arms of the support assembly 24, the adapter assembly 22, and/or the dome 20 (e.g., via the handles 52). However, it is contemplated that remote-controlled functionality could also be used (e.g., remotely controlled arms of the support assembly 24). The arms of the support assembly 24 may be covered by a sheath or the joints may be exposed.

In some embodiments, the system 10 may include a mobile base 70, as shown in FIGS. 2 and 3, to which the support assembly 24 is attached and which permits the system 10 to be at least partially mobile. The mobile base 70 may include a platform with a plurality of wheels (e.g., roller wheels, casters, etc.). The mobile base 70 permits the system 10 to be moved from various areas (e.g., room to room or suite to suite) for multiple patients, as needed, or into a medical operating room. The mobile base 70 may itself be adjustable, including height adjustments as needed in coordination with adjustment of the position of the support assembly 24 to position the dome 20 as needed for positioning over the body area of each patient for each given medical procedure.

In alternative embodiments, the support assembly 24 of the system 10 may be attached to a medical chair or bed on which the patient is located while undergoing a medical procedure (e.g., being attached to the dental chair 14, as shown in FIG. 11). In further embodiments, the support assembly 24 of the system 10 may be affixed in a semi-permanent location, such as to a medical station (e.g., a dental cabinet that provides dental tools, e.g., water picks, air picks, drills, brushes, etc., necessary for dental work or oral surgeries). In still further embodiments, the support assembly 24 of the system 10 may be affixed to other permanent fixtures, such as to the wall or ceiling of a room or suite of a medical facility.

Finally, as illustrated in FIG. 2, the system 10 may include a control system 80 configured to provide control and power to components of the system 10. For example, the control system 80 may provide electrical power to the fans 42 of the adapter assembly 22. The control system 80 may also provide electrical power to other components of the system 10 that require such power. For instance, in embodiments of the system that include a UV light filter, the control system 80 may provide electrical power to such UV light filter. In addition, the system 10 may include one or more visual lights for providing light onto the patient during medical procedures. Such lights may comprise light-emitting diode or other types of visible light emitters, and may be positioned on or integrated with the dome 20 and/or the adapter assembly 22. The lights may be positioned underneath the dome 20, but may also be positioned to shine through the dome. The control system 80 may provide electrical power to such visual lights. The control system 80 may receive power externally, such as via a cable that can be plugged into a facility's mains power. In some embodiments, however, the control system 80 may include a rechargeable battery, which permits the system 10 to operate when mains power is unavailable or would otherwise be inconvenient.

In some embodiments, the control system 80 may provide automated control over various elements of the system 10. In such embodiments, the control system 80 may include a computing device comprising one or more processing elements and/or memory elements necessary to effectuate such automated control. The control system 80 may be in communication via one or more wires or cables to facilitate such control, as well as to transfer electrical power to elements of the system 10. However, in some embodiments, some such control or power transfer may be performed wirelessly.

In use, the dome 20 is configured to be positioned above an intended body area of a patient while a medical procedure is performed on the body are of the patient. As illustrated in FIG. 1, for instance, the dome 20 may be positioned above the patient's 12 head or oral cavity area, while a patient is seated and angled horizontally during a dental procedure. The inner surface 30 of the dome 20 (i.e., the concave surface) faces the patient 12, while the outer surface 32 (e.g., the convex surface) faces the dental provider. Preferably, during such a dental procedure, the dome 20 is configured to be positioned over and cover the patient's 12 face, and possibly the entire area of the patient's 12 head. The clear/transparent material from which the dome 20 is formed allows the dental provider to see through the dome and reach under the dome 20 edge 36 into the patient's mouth while carrying out the procedures. Thus, it will be appreciated that the dome 20 is not typically configured to itself come into contact with the patient's 12 face, but remains above the patient's 12 face as a barrier. The dental provider's own face, likewise, remains on the other side of the dome 20 (but not in contact with the dome 20 per se) such that the dome 20 is operable to block and contain the spray of any aerosols vertically from the patient's 12 mouth or nose as well as horizontally to the sides. In this way, the dome 20 also minimizes the travel of aerosols throughout the dental office. The provider's ability to view the patient's mouth and move freely outside the dome 20 is not obstructed. Beneficially, the transparent dome 20 can be easily sterilized, changed out, disposed of, and/or replaced in between each use (e.g., via the elements of the latching unit previously described).

As was described above, the dome 20 will generally be positioned above an intended body area of a patient so as to collect aerosols emitted from the patient, thereby reducing aerosols exposed to medical personnel and/or dispersed into the environment. Notably, the open end of the dome 20 is positioned above (e.g., spaced above or apart) from the intended body area of the patient. As such, the system 10 (including the dome 20) will generally not be closed or sealed around the body area of the patient. For instance, the system 10 (including the dome 20) will generally not be fully enclosed or sealed around the head, face, or mouth, of a patient during a dental procedure. As a result, the medical personnel performing the medical procedure (e.g., the dental procedure) can extend her hands underneath the dome 20, e.g., between the dome 20 and the intended body area (e.g., the head, face, and/or mouth) of the patient, so as to perform the medical procedure while the dome 20 is in place above the intended body area of the patient. Nevertheless, the system 10 will still be configured to reduce aerosols emitted from the patient due to (i) the shape of the dome 20 (e.g., the bowl shape) being configured to collect such aerosols, and/or (ii) the fans 42 being configured to generate negative air pressure under the dome 20 such that the dome can draw in and collect such aerosols.

In view of the above, embodiments of the present invention include methods of using an aerosol reduction system during a medical procedure. Such a method may include the steps of providing a system 10 comprising a transparent dome 20, an adapter assembly 22 configured to releasably support the dome 20, and a support assembly 24 configured to support the adapter assembly 22 and the dome 20. Such a method may additionally include the step of actuating the support assembly 24 such that the dome 20 is positioned over an intended body area of a patient. The method may further include the step of blocking, via the dome 20, aerosols emitted from the body area of the patient. For instance, as described above, the intended body area of the patient may be a head, face, or oral cavity of a patient 12, and the medical procedure may be a dental procedure (e.g., oral surgery).

As was described above, the adapter assembly 22 may, in some embodiments, include one or more fans 42 for creating a negative air pressure underneath the dome 20 adjacent to the edge 36 of the dome 20. As such, the fans 42 can draw air and/or any aerosols emitted from the patient's 12 mouth or nose through the adapter assembly 22 where it can be captured or filtered before contaminating the dental provider or the dental office. In certain embodiments, the dome 20 may include no holes or apertures for ventilation or any other air movement (i.e., it is a monolithic, uninterrupted body). In alternative embodiments, the dome 20 may be configured to include a suction tube line for pulling the aerosol spray from the patient's mouth up into the dome 20. It will be appreciated that this could be integrated as part of existing extraoral suction lines present on some dental cabinets.

Furthermore, in some embodiments, a drape may be affixed to the edge 36 of the dome 20 and hang down over the patient's 12 body to further confine the aerosols within the dome 20. The drape may be made of paper or waxed material, such as used for patient dental bibs. Ideally, the drape may be disposable for each patient. In any event, even with the drape, the dome 20 remains substantially open to a free flow of ambient air such that the patient's 12 own air flow is not restricted under the dome 20.

Additional advantages of the various embodiments of the invention will be apparent to those skilled in the art upon review of the disclosure herein. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein. For example, the dome is not limited specifically to circular or annual domes, but encompasses polygonal cross sections or cross sections presenting other geometric shapes (e.g., oval or elliptical cross sections).

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

Further, the description of the embodiments disclosed herein may refer to various relative orientations, such as lower, upper, horizontal, vertical, above, below, up, down, bottom, top, and the like. These terms are used for convenience of description and are not intended to limit the scope of the invention in any way. Unless stated otherwise, these relative terms do not require the equipment to be constructed or operated in a particular orientation. Likewise, terms such as attached, connected, coupled, interconnected, and the like are used to mean structures that may be directly or indirectly attached to each other including in a movable or rigid attachment or relationship.

All terms used herein are to be broadly interpreted unless otherwise stated. For example, the terms "processor," "processing element," and the like, as used herein, may, unless otherwise stated, broadly refer to any programmable system including systems using central processing units, microprocessors, microcontrollers, reduced instruction set circuits (RISC), application specific integrated circuits (ASIC), logic circuits, and any other circuit or processor capable of executing the functions described herein. The above examples are illustrative only, and are thus not intended to limit in any way the definition and/or meaning of the term "processor." In particular, a "processor" may include one or more processors individually or collectively performing the described operations. In addition, the terms "software," "computer program," and the like, may, unless otherwise stated, broadly refer to any executable code stored in memory for execution on mobile devices, clusters, personal computers, workstations, clients, servers, and a processor or wherein the memory includes read-only memory (ROM), electronic programmable read-only memory (EPROM), random access memory (RAM), erasable electronic programmable read-only memory (EEPROM), and non-volatile RAM (NVRAM) memory. The above described memory types are examples only, and are thus not limiting as to the types of memory usable for storage of a computer program.

The term "memory," "memory area," "memory element," "storage device," and the like, as used herein, may, unless otherwise stated, broadly refer to substantially any suitable technology for storing information, and may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others.

The terms "computer," "computing device," "computer system," and the like, as used herein, may, unless otherwise stated, broadly refer to substantially any suitable technology for processing information, including executing software, and may not be limited to integrated circuits referred to in the art as a computer, but may broadly refer to a microcontroller, a microcomputer, a programmable logic controller (PLC), an application specific integrated circuit, and other programmable circuits, and these terms are used interchangeably herein.

Although the invention has been described with reference to the one or more embodiments illustrated in the figures, it is understood that equivalents may be employed and substitutions made herein without departing from the scope of the invention as recited in the claims.

Having thus described one or more embodiments of the invention, what is claimed as new and desired to be protected by Letters Patent includes the following:

1. A system for reducing aerosols emitted from a patient on which a medical procedure is being performed, said system comprising:
   a transparent dome including an annular bottom perimeter;
   an adapter assembly configured to releasably support said dome, wherein said adapter assembly comprises a housing enclosing an interior space, and wherein said housing supports at least one baffle, at least one filter, and at least one fan,
   wherein said adapter assembly comprises an opening forming an inlet to the interior space of said housing, wherein the opening is positioned below said dome, such that said fan can create a negative air pressure underneath said dome so as to draw air and aerosols present below said dome through said baffle and said filter,
   wherein said baffle comprises a curved plate with a shape that matches the annular bottom perimeter of said dome; and
   a support assembly configured to support said adapter assembly and said dome, wherein said support assembly is adjustable such that said dome can be selectively positioned over an intended body area of the patient and block aerosols emitted from the intended body area.

2. The system of claim 1, wherein said dome is formed from plastic.

3. The system of claim 1, wherein said dome comprises an open-ended shell having a shape in the form of a partial sphere, wherein an inner surface of said dome has a concave shape and an outer surface of said dome has a convex shape.

4. The system of claim 3, wherein said annular bottom perimeter has a diameter of between 12 and 45 inches.

5. The system of claim 4, wherein said dome has a height, as measured from the annular bottom perimeter to an apex of the outer surface, of between 6 and 30 inches.

6. The system of claim 3, wherein said dome has a thickness of between 0.004 and 0.4 inches.

7. The system of claim 1, wherein said filter comprises high-efficiency particulate air (HEPA) filters.

8. The system of claim 1, wherein said filter comprises carbon-based filters.

9. The system of claim 1, wherein said adapter assembly comprises one or more UV lights configured to disinfect the air flowing through the interior space.

10. The system of claim 1, wherein said adapter assembly comprises a latching unit for releasably securing said dome to said adapter assembly.

11. The system of claim 10, wherein said latching unit includes a bracket assembly, wherein said bracket assembly is configured to secure said adapter assembly to said support assembly.

12. The system of claim 10, wherein said bracket assembly includes one or more handles configured to permit a user to adjust the position of said dome.

13. The system of claim 1, wherein said support assembly comprises one or more articulating arms configured such that a position of said dome can be shifted vertically and rotated about one or more rotational axes.

14. The system of claim 13, wherein said support assembly is supported on a mobile base, such that said system is portable.

15. The system of claim 13, wherein said support assembly is supported on a medical chair or bed on which the patient is located for the medical procedure.

16. The system of claim 1, further comprising a control system for controlling one or more electronic features of the system, wherein control system includes a rechargeable battery.

17. A method of using an aerosol reduction system during a medical procedure, said method comprising the steps of:
   (a) providing a system comprising— a transparent dome including an annular bottom perimeter, an adapter assembly configured to releasably support the dome, wherein the adapter assembly comprises a housing enclosing an interior space, and wherein the housing supports at least one baffle, at least one filter, and at least one fan, wherein the adapter assembly comprises an opening forming an inlet to the interior space of the housing, wherein the opening is positioned below the dome, such that the fan can create a negative air pressure underneath the dome so as to draw air and aerosols present below the dome through the baffle and the filter, wherein the baffle comprises a curved plate with a shape that matches the annular bottom perimeter of the dome, a support assembly configured to support the adapter assembly and the dome, wherein the support assembly is adjustable such that the dome can be selectively positioned over an intended body area of a patient and block aerosols emitted from the intended body area; and (b) actuating the support assembly such that the dome is positioned over the intended body area of the patient; and (c) blocking, via the dome, aerosols emitted from the body area of the patient.

18. The method of claim 17, wherein the intended body area of the patient is a head of the patient, and wherein the medical procedure is a dental procedure.

* * * * *